(12) United States Patent
Hawkes et al.

(10) Patent No.: US 6,459,263 B2
(45) Date of Patent: Oct. 1, 2002

(54) NUCLEAR MAGNETIC RESONANCE MEASUREMENTS IN WELL LOGGING USING MOTION TRIGGERED PULSING

(75) Inventors: Robert Hawkes, Cambridge; Robert Slade, Oxfordshire; Alun Lucas, Hertfordshire, all of (GB)

(73) Assignees: Baker Hughes Incorporated, Houston, TX (US); Oxford Instruments Superconductivity Ltd., Eynsham (GB)

( * ) Notice: Subject to any disclaimer, the term of this patent is extended or adjusted under 35 U.S.C. 154(b) by 0 days.

(21) Appl. No.: 09/778,295

(22) Filed: Feb. 6, 2001

Related U.S. Application Data (60) Provisional application No. 60/180,982, filed on Feb. 8, 2000.

(51) Int. Cl.$^7$ .................................................. G01V 3/00
(52) U.S. Cl. ......................................... 324/303; 324/300
(58) Field of Search ............................... 324/303, 300, 324/307, 309, 312, 314, 322, 318

(56) References Cited

U.S. PATENT DOCUMENTS

| | | | |
|---|---|---|---|
| 4,773,263 A | 9/1988 | Lesage et al. | 73/151 |
| 5,023,551 A | 6/1991 | Kleinberg et al. | 324/303 |
| 5,141,061 A | 8/1992 | Henneuse | 175/56 |
| 5,358,059 A | 10/1994 | Ho | 175/45 |
| 5,363,041 A | 11/1994 | Sezginer | 324/303 |
| 5,381,092 A | 1/1995 | Freedman | 324/303 |
| 5,705,927 A | 1/1998 | Sezginer et al. | 324/303 |
| 5,784,273 A | 7/1998 | Madhavan | 364/176 |
| 5,864,058 A | 1/1999 | Chen | 73/152.47 |
| 5,977,768 A * | 11/1999 | Sezginer et al. | 324/303 |
| 6,008,646 A * | 12/1999 | Griffin et al. | 324/303 |
| 6,268,726 B1 * | 7/2001 | Prammer et al. | 324/303 |

FOREIGN PATENT DOCUMENTS

| | | | |
|---|---|---|---|
| EP | 0 581 666 | * | 2/1994 |
| EP | 0649 035 | * | 4/1995 |
| WO | WO97/34167 | | 9/1997 |
| WO | WO99/36801 | | 7/1999 |
| WO | WO 99/36801 | * | 7/1999 |

OTHER PUBLICATIONS

Edwin D. Becker et al.; Driven Equilbrium Fourier Transform Spectroscopy, A New Method for Nuclear Magnetic Resonance Signal Enhancement, 5th Western Regional Meeting of the American Chemical Society, Anaheim, CA, Oct. 7, 1969.

R.R. Ernst et al; Application of Fourier Transform Spectroscopy to Magnetic Resonance, The Review of Scientific Instruments, pp. 93–102.

C.P. Slichter; *Principles of Magnetic Resonance*, 1989, pp. 38–45.

* cited by examiner

Primary Examiner—Edward Lefkowitz
Assistant Examiner—Brij B. Shrivastav
(74) Attorney, Agent, or Firm—Madan, Mossman & Sriram, P.C.

(57) ABSTRACT

A pulsed NMR tool has a magnet arrangement that is used to generate a static magnetic field having a substantially uniform field strength in a region of the formation surrounding the borehole. An RF coil is used to produce pulsed RF fields orthogonal to the static field in the region of examination. The nuclear spins in the formation align themselves along the externally applied static magnetic field. A pulsed RF field is applied to tip the spins by 90°, resulting in a precession of the spins. The tipping pulse is followed by a series of refocusing pulses and the resulting series of pulse echoes is detected. Motion sensors on the tool produce signals indicative of the motion of the tool and a processor on the tool controls the timing of the tipping pulse to coincide with substantially zero motion of the tool in an axial direction or one perpendicular to the axial direction. A Kalman filter or other predictive filter is used to predict the desirable pulse triggering times.

17 Claims, 4 Drawing Sheets

NUCLEAR MAGNETIC RESONANCE MEASUREMENTS IN WELL LOGGING USING MOTION TRIGGERED PULSING

CROSS REFERENCES TO RELATED APPLICATIONS

This application claims priority from U.S. Provisional Patent Application Ser. No. 60/180,982 filed on Feb. 8, 2000.

BACKGROUND OF THE INVENTION

1. Field of the Invention

This invention relates generally to determining geological properties of subsurface formations using Nuclear Magnetic Resonance ("NMR") methods for logging wellbores, particularly for improving the accuracy of the NMR signals by making measurements at times when the effect of tool motion is likely to be small.

2. Background of the Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as nuclear spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a uniform or near uniform static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied static magnetic field creating a net magnetization. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p / 2 \qquad (1)$$

where γ is the gyromagnetic ratio, $B_1$ is the effective field strength of the oscillating field and $t_p$ is the duration of the RF pulse.

After tipping, the spins precess around the static field at a particular frequency known as the Larmor frequency $\omega_0$ given by $$\omega_0 = \gamma B_0 \qquad (2)$$

where $B_0$ is the static field strength. At the same time, the magnetization returns to the equilibrium direction (i.e., aligned with the static field) according to a decay time known as the "spin-lattice relaxation time" or $T_1$. For hydrogen nuclei $\gamma/2\pi$=4258 Hz/Gauss, so that a static field of 235 Gauss, would produce a precession frequency of 1 MHz. T1 is controlled totally by the molecular environment and is typically ten to one thousand ms. in rocks.

At the end of a θ=90° tipping pulse, spins on resonance are pointed in a common direction perpendicular to the static field, and they precess at the Larmor frequency. However, because of inhomogeneity in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. This de-phasing occurs with a time constant that is commonly referred to as $T_2^*$ if it is predominantly due to the static field inhomogeneity of the apparatus, and as $T_2$ if it is due to properties of the material.

The receiving coil is designed so that a voltage is induced by the precessing spins. Only that component of the nuclear magnetization that is precessing in the plane perpendicular to the static field is sensed by the coil. After a 180° tipping pulse (an "inversion pulse"), the spins on resonance are aligned opposite to the static field and the magnetization relaxes along the static field axis to the equilibrium direction. Hence, a signal will be generated after a 90° tipping pulse, but not after a 180° tipping pulse in a generally uniform magnetic field.

While many different methods for measuring $T_1$ have been developed, a single standard known as the CPMG sequence (Carr-Purcell-Meiboom-Gill) for measuring $T_2$ has evolved. In contrast to laboratory NMR magnets, well logging tools have inhomogeneous magnetic fields due to the constraints on placing the magnets within a tubular tool and the inherent "inside-out" geometry. Maxwell's divergence theorem dictates that there cannot be a region of high homogeneity outside the tool. Therefore in typical well bores, $T_2^* \ll T_2$, and the free induction decay becomes a measurement of the apparatus-induced inhomogeneities. To measure the true $T_2$ in such situations, it is necessary to cancel the effect of the apparatus-induced inhomogeneities. To accomplish the same, a series of pulses is applied to repeatedly refocus the spin system, cancelling the T2* effects and forming a series of spin echoes. The decay of echo amplitude is a true measure of the decay due to material properties. Furthermore it can be shown that the decay is in fact composed of a number of different decay components forming a T2 spectrum. The echo decay data can be processed to reveal this spectrum which is related to rock pore size distribution and other parameters of interest to the well log analyst.

One method to create a series of spin echoes is due to Carr and Purcell. The pulse sequence starts with a delay of several T1 to allow spins to align themselves along the static magnetic field axis. Then a 90° tipping pulse is applied to rotate the spins into the transverse plane where they precess with angular frequency determined by local magnetic field strength. The spin system loses coherence with time constant, T2*. After a short time $t_{CP}$ a 180° tipping pulse is applied which continues to rotate the spins, inverting their position in the transverse plane. They continue to precess, but now their phases converge until they momentarily align a further time $t_{CP}$ after the 180° pulse. The 180° pulse is re-applied after a further time $t_{CP}$ and the process repeated many times forming a series of spin echoes with spacing $2 t_{CP}$.

While the Carr-Purcell sequence would appear to provide a solution to eliminating apparatus induced inhomogeneities, it was found by Meiboom and Gill that if the duration of the 180° pulses in the Carr-Purcell sequence were even slightly erroneous so that focusing is incomplete, the transverse magnetization would steadily be rotated out of the transverse plane. As a result, substantial errors would enter the T2 determination. Thus, Meiboom and Gill devised a modification to the Carr-Purcell pulse sequence such that after the spins are tipped by 90° and start to de-phase, the carrier of the 180° pulses is phase shifted by π/2 radians relative to the carrier of the 90° pulse. This phase change causes the spins to rotate about an axis perpendicular to both the static magnetic field axis and the axis of the tipping pulse. For an explanation, the reader is referred to a detailed account of spin-echo NMR techniques, such as "NMR: a nuts and bolts approach", Fukushima and Roeder. As a result any error that occurs during an even numbered pulse of the CPMG sequence is cancelled out by an opposing error in the odd numbered pulse. The CPMG sequence is therefore tolerant of imperfect spin tip angles. This is especially useful in a well logging tool which has inhomogeneous and imperfectly orthogonal static and pulse-oscillating (RF) magnetic fields.

U.S. Pat. No. 5,023,551 issued to Kleinberg discloses an NMR pulse sequence for use in the borehole environment which combines a modified fast inversion recovery (FIR) pulse sequence with a series of more than ten, and typically hundreds, of CPMG pulses according to $$[W_i-180-\tau_i-90-(t_{cp}-180-t_{cp}-\text{echo})_j]_i \quad (3)$$

where j=1,2, . . . ,J, and J is the number of echoes collected in a single CPMG sequence, where i=1,2, . . . ,I and I is the number of waiting times used in the pulse sequence, where $W_i$ are the recovery times before the inversion pulse, and where $\tau_i$ are the recovery times before a CPMG sequence, and where $t_{CP}$ is the Carr-Purcell spacing. The phase of the RF pulses 90 and 180 is denoted by the subscripts X and Y, Y being phase shifted by π/2 radians with respect to X. The subscripts also conventionally relate to the axis about which rotation of the magnetization occurs during the RF pulse in a local Cartesian coordinate system centered on the nucleus in which the static magnetic field is aligned in the Z direction and the RF field in the X direction. This sequence can be used to measure both T1 and T2, but is very time consuming, limiting logging speed. If $t_{CP}$ is set to zero and the inverting pulse is omitted then the sequence defaults to standard CPMG for measuring T2 only.

Tool motion can seriously affect the performance of NMR tools used in an MWD environment. NMR tools that have static and magnetic fields that have complete rotational symmetry are unaffected by rotation of the tool since the fields in the region of examination do not change during the measurement sequence. However, any radial or vertical component of tool motion due to vibration will affect the NMR signal. U.S. Pat. No. 5,389,877 issued to Sezginer describes a truncated CPMG sequence in which the sequence duration and recovery delay are so short that only signals from the clay and capillary bound fluids are detected. A truncated sequence has the advantage that the effect of tool motion on the measurements is reduced due to the short measurement time (approx. 50 ms., compared to greater than 300 ms. for normal downhole CPMG measurements.) As discussed in U.S. Pat. No. 5,705,927 issued to Kleinberg, resonance regions of many prior art instruments are of the order of 1 mm. Accordingly, a lateral vibration at a frequency of 50 Hz having an amplitude of 1 mm (100 g acceleration) would disable the instrument. The Kleinberg '927 patent discloses making the length of each CPMG sequence small, e.g. 10 ms, so that the drill collar cannot be displaced by a significant fraction of the vertical or radial extent of the sensitive region during a CPMG pulse sequence. However, as noted above, using such short sequences and short wait times only gives an indication of the bound fluid volume and gives no indication of the total fluid volume.

There are numerous patents discussing the vibration of a rotating shaft subject to mechanical forces of the kind encountered by a drill string. U.S. Pat. No. 5,358,059 issued to Ho discloses the use of multiple sensors, including accelerometers, magnetometers, strain gauges and distance measuring sensors for determining the conditions of a drillstring in a borehole in the earth. The motion of the drill string in the borehole is characterized by vertical motion, rotational motion and a swirl of the drill string. Whirling of the drillstring is the eccentric motion of the axis of the drillstring around the axis of the borehole and is a motion of great concern in NMR measurements. In an NMR tool, this means that the magnetic field strength in the region of examination changes with time, thereby affecting the amplitudes and shapes of the pulse echos. When the whirl is zero, a tool that has complete rotational symmetry would be insensitive to rotational movement of the drillstring and the tool.

The vertical movement, including vertical vibration, of the tool also causes errors in the NMR measurements when the region of examination is of limited vertical extent: any vertical motion will again result in a time dependence in the tool's static magnetic field as seen by the nuclear spins in the formation fluids and thus affect the shape and amplitude of the spin echos.

It would therefore be desirable to have an NMR tool that is less sensitive to motion of the tool, particularly to vertical motion and to swirling motion of a drill string. The present invention satisfies this need.

SUMMARY OF THE INVENTION

The present invention is a method of improving the NMR signals received from a formation surrounding a borehole. Any pulsed NMR tool in which a magnet arrangement is used to generate a static magnetic field having a substantially uniform field strength in a region of the formation surrounding the borehole, and in which an RF coil is used to produce pulsed RF fields substantially orthogonal to the static field in the region of examination may be used. The nuclear spins in the formation align themselves along the externally applied static magnetic field. A pulsed RF field is applied to tip the spins on resonance by 90°. Sensors on the tool monitor the motion of the tool and a processor on the tool triggers the tipping pulse when the whirling motion of the tool is at a minimum. In one embodiment of the invention, conventional CPMG pulse sequences are used. In an alternate embodiment of the invention, a refocusing pulse having a spin tip angle substantially less than 180° is applied with phase shifted by π/2 radians with respect to the 90° tipping pulse. Although the refocusing pulses result in a spin tip angle that is substantially less than 180°, their bandwidth is closer to that of the original 90° pulse. Hence more of the nucleii originally tipped by 90° are refocused, resulting in larger echoes, typically by 15–25%, than would be obtained with a conventional 180° refocusing pulse and less RF power consumption. One embodiment of the invention uses a −90° recovery pulse at the end of the sequence to speed up the recovery of the pulses and their realignment with the static field at the end of the pulse sequence and to allow cancellation of the 90° degree "ring-down" artifact. These echoes are analyzed in a conventional manner to give the NMR parameters of the formation.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein.

DETAILED DESCRIPTION OF PREFERRED EMBODIMENTS

Figure 1A:
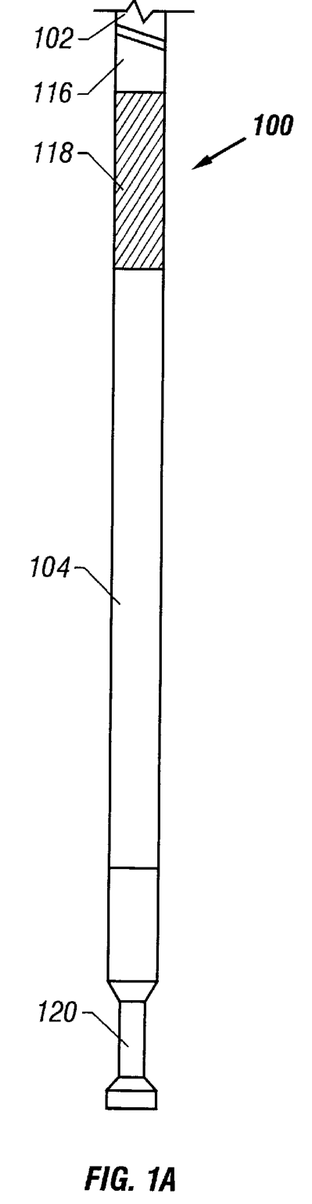
FIGS. 1A–1C are side elevational views partially in section (see FIG. 1A) of a an exemplary drilling assembly including an NMR tool.
Figure 1B:
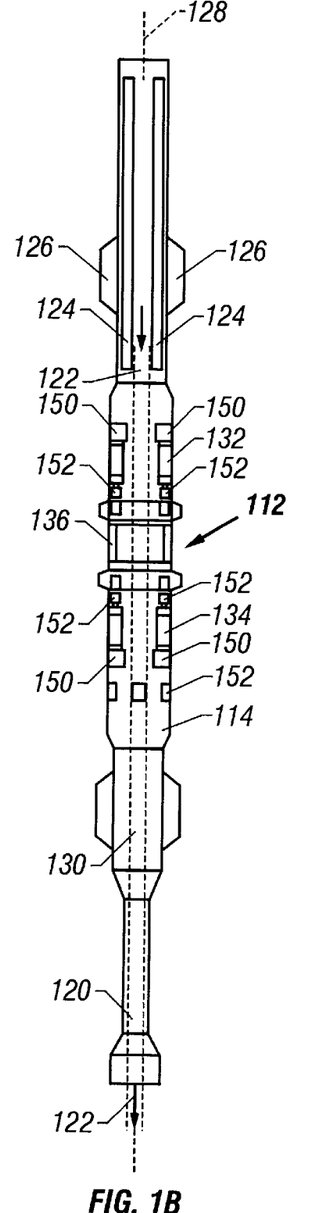
Figure 1C:
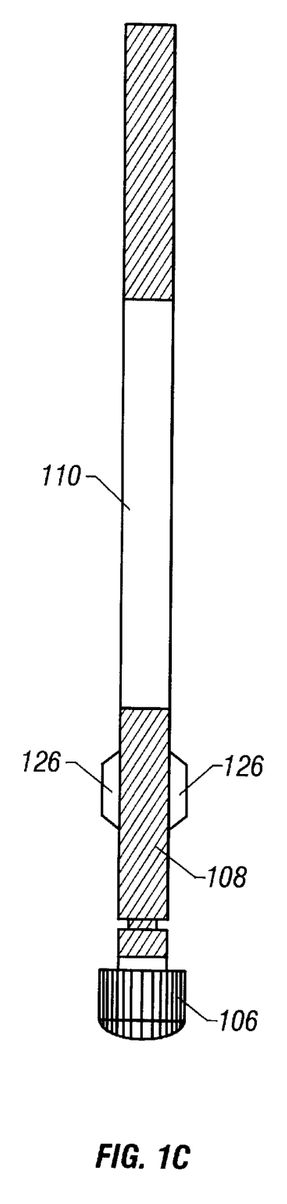

Referring to FIGS. 1A–1C, an exemplary drilling assembly 100 at the end of a drill string 102 or coiled tubing is illustrated. A measurement-while-drilling (MWD) tool 104, an associated pulsed nuclear magnetic resonance (NMR) tool 112 (contained within a housing 114) and electronic circuitry 124, and a pulsed power unit 118 are connected in tandem in the drilling assembly 100. Flex subs 120 are used for example in connecting the MWD tool 104 and the NMR tool 112 in the drilling assembly 100. The MWD tool 104 may also include a sonic sensor, a density measurement tool, and a porosity measurement tool. A communication sub 116 using, for example, two-way telemetry, is also provided as illustrated in the drilling assembly 100. The drilling assembly is also provided with a plurality of motion sensors 152 for sensing the motion of the tool within the borehole. In a preferred embodiment of the invention, the motion sensors are accelerometers that sense the three components of acceleration of the tool.

The drilling assembly 100 includes a drill bit 106, bearing assembly 108, and downhole mud motor 110. The drill string 102 includes, for example, sections of drill pipe connected end-to-end or a generally continuous coiled. The borehole typically contains a drilling fluid 122 or "mud" which is forced through the drill string 102 and the bottom hole drilling assembly 100 through the drill bit 106. A channel 130 within the drill string 102 and drilling assembly 100 allows the drilling fluid 122 through the drill string 102 and drilling assembly 100. The drilling fluid acts to lubricate the drill bit 106 and to carry borehole cutting or chips away from the drill bit 106.

The communication sub 116, power unit 118, MWD tool 104, and NMR tool 112 are all connected in tandem with the drill string 102. Such subs and tools form a bottom hole drilling assembly 100 between the drill string 102 and the drill bit 106. Stabilizers 126 are used to stabilize and center the drilling assembly 100 and tools within the borehole. The housing 114, for example, a drilling collar, is made of a nonmagnetic alloy. The drilling assembly 100 makes various measurements including pulsed nuclear magnetic resonance measurements while the borehole is being drilled. As seen in FIG. 1B, the NMR tool is rotationally symmetric about a longitudinal axis 128 of the drilling assembly 100.

Figure 2:
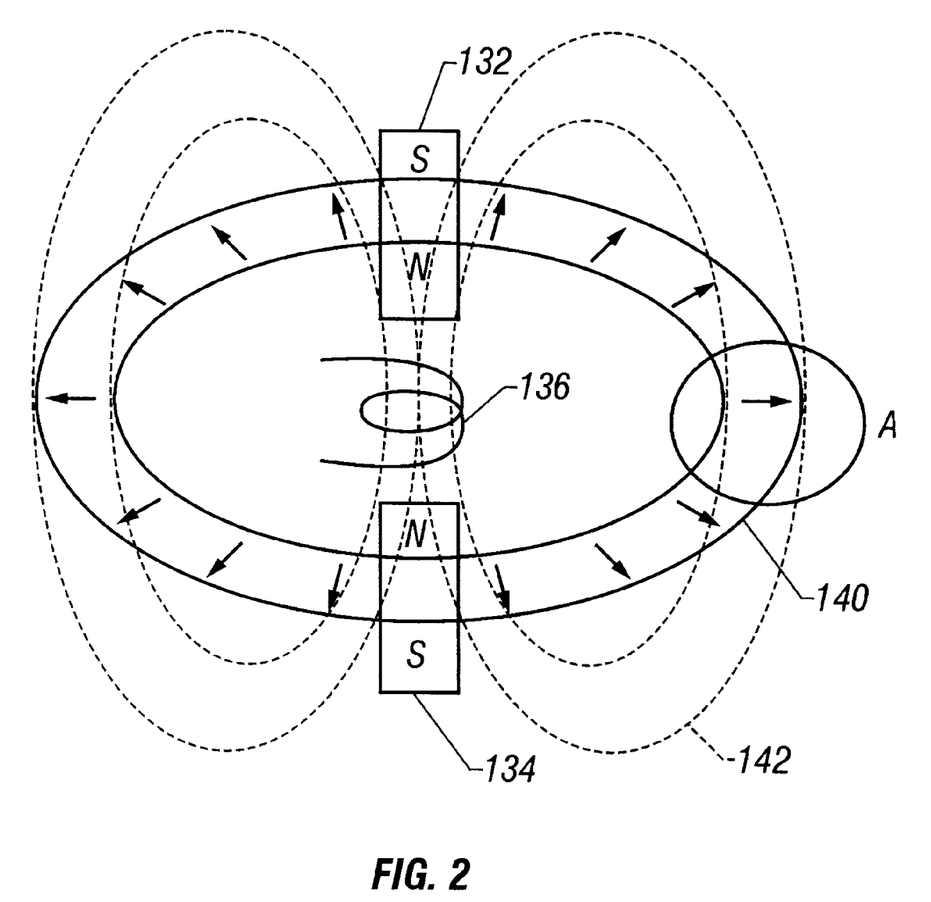
FIG. 2 (PRIOR ART) illustrates the production of a toroidal region of homogeneous radial magnetic field perpendicular to a pair of axially aligned magnets having like adjacent poles and the application of a pulsed RF field to the magnetization.
Figure 4:
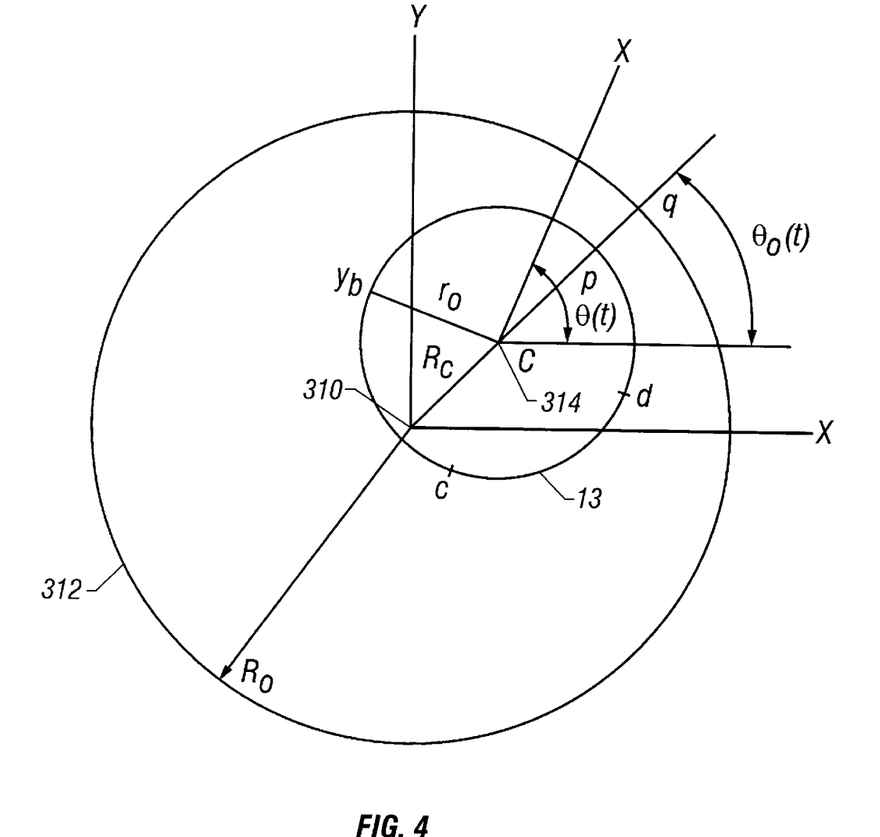
FIG. 4 shows the geometry of whirl motion of a tool in a borehole.
Figure 5:
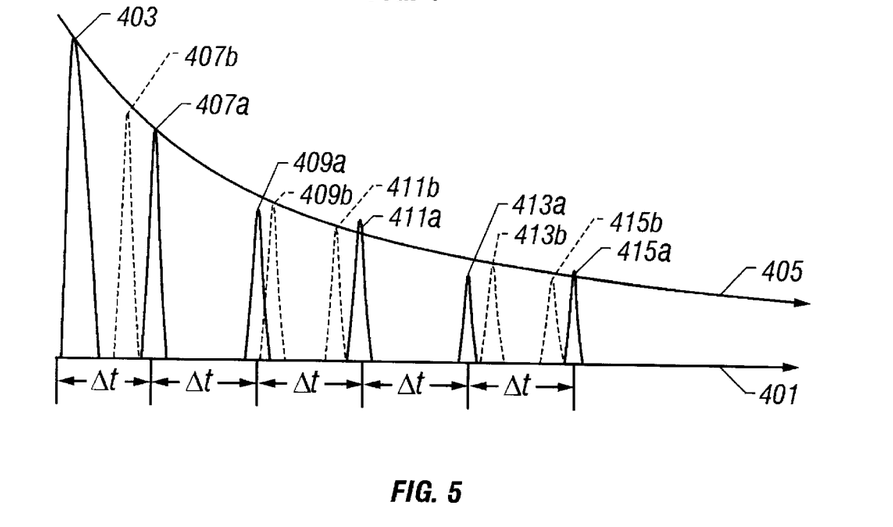
FIG. 5 is a schematic illustration of the use of nonuniform times for the refocusing pulses based upon measured tool motion.

In the preferred embodiment, pulsed NMR tool 112 includes at least two spaced-apart magnets 132 and 134 housed in the drilling assembly 100 and within the NMR tool 112 for producing a static magnetic field having a region of substantially uniform magnetic intensity in the vicinity of the borehole. The at least two spaced-apart magnets 132 and 134 illustrated in FIGS. 2, 4 and 5 are tubular in shape and arranged coaxially within the NMR tool 112 and to surround the channel 130. A radio frequency (RF) transmitting antenna or coil 136 also surrounds the channel 130 and is located, for example, between the two spaced-apart magnets 132 and 134. The RF coil 136 is connected to a suitable RF pulse transmitter such as the pulsed power unit 118 for providing power at selected frequencies and a processor 124 which drives the RF transmitting antenna or RF coil 136. The RF coil 136 is pulsed and creates a high frequency RF field orthogonal to the static magnetic field. The processor also receives the signals from the sensors indicative of the motion of the tool. As discussed below with reference to FIG. 6, the processor controls the timing of the pulse sequence on the basis of the signals from the motion sensors.

The at least two magnets 132 and 134 are permanently magnetized, for example, in the axial direction and, in one embodiment, are positioned in opposing directions, as shown in FIG. 2. As shown in FIG. 2, like magnetic poles, for example, the north magnetic poles of the two magnets 132 and 134 face one another for producing a toroidal region of homogeneous radial magnetic field 140 perpendicular to the pair of axially aligned magnets 132 and 134. The pulsed RF coil 136 creates the pulsed RF field 142 illustrated by dashed lines. The distance of the toroidal region 140 of homogeneous radial magnetic field from the axis of the magnets 132 and 134 is dependent upon the strength of the magnets 132 and 134 and the distance between like poles of the magnets 132 and 134. Rock pores (not shown) in the earth formations are filled with fluid, typically water or hydrocarbon. The hydrogen nuclei in the fluid are aligned in the region of homogeneous magnetic field 140, generated by the magnets 132 and 134. The hydrogen nuclei are then tipped away from the homogeneous magnetic field 140 by the pulsed RF field 142 produced by RF coil 136. At the termination of the pulsed RF field from RF coil 136, the hydrogen nuclei revolve or precess at high frequency around the homogeneous magnetic field 140 inducing an NMR signal in the RF coil 136 until the hydrogen nuclei relax to the original direction along the homogeneous magnetic field 140. The induced NMR signals are sent to the surface for processing or can be processed by a downhole processor (not shown).

Other configurations of magnets could also be used. For example, U.S. Pat. No. 4,710,713 issued to Shtrikman discloses a magnet arrangement in which the static field is produced by cylindrical magnets that have the north and south poles on the curved faces of the magnets, resulting in a static field of dipole shape. The Strikman patent uses a rectangular loop antenna to produce a radio frequency field of similar dipole shape, but rotated by 90 degrees with respect to the static field, thus maintaining the orthogonality between the static field and the RF field. Other variations would be known to those versed in the art, and any of these could be used in the present invention.

Figure 3A:
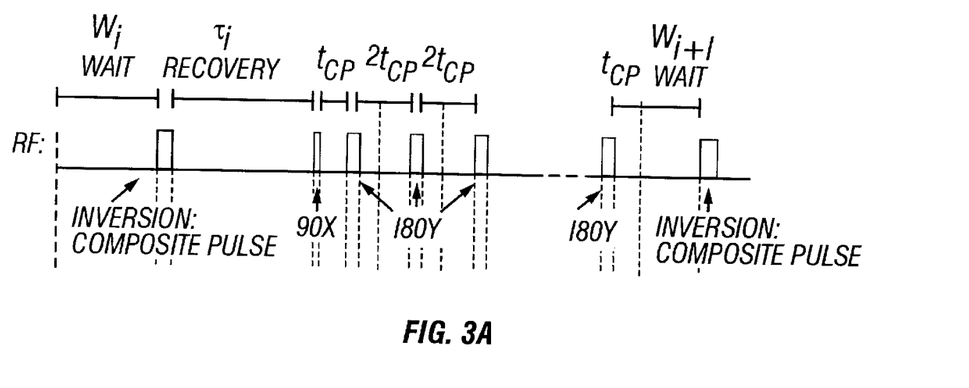
FIGS. 3a–3c (PRIOR ART) are graphs over time respectively of the pulse sequence of a prior art invention, and the resulting longitudinal magnetization and measurable signal.
Figure 3B:
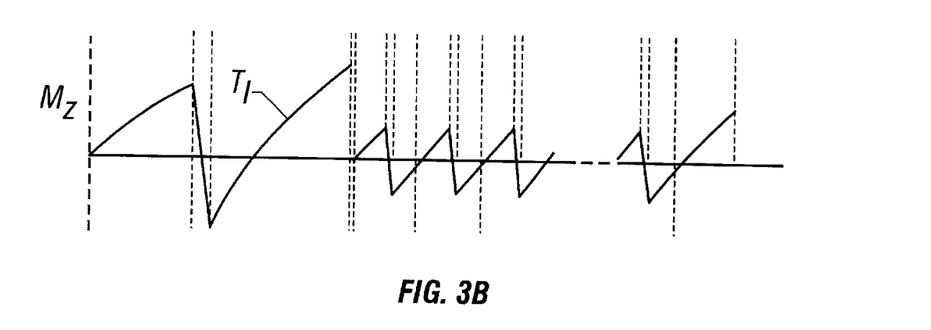
Figure 3C:
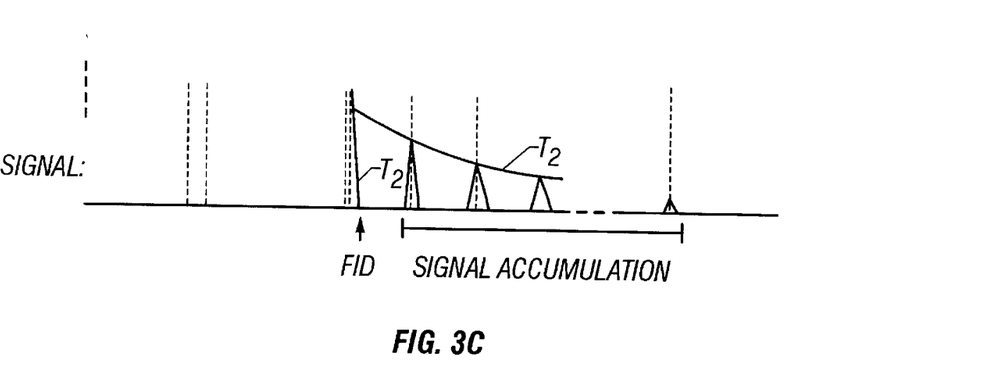

Turning to FIGS. 3a–3c, (PRIOR ART) the pulse sequence set forth by (3) above is seen in graphical form. At the start of any (e.g. i-th) sequence after waiting for a waiting period $W_i$ the spin system is at zero transverse magnetization (as seen in FIG. 3c) and at a positive longitudinal magnetization which is less than the full equilibrium magnetization (as seen in FIG. 3b). When a pulse of 180° degrees is applied, the spins are inverted. However, no signal is observed during this time period, because the spins are along the static field and do not induce any signal in a measurement coil of the borehole tool. After the 180° degree pulse, and during the so-called recovery time $\tau_i$ the nuclear magnetization of the formation under investigation begins to relax towards the direction dictated by the static field. The rate at which a magnetization returns toward the static field is governed by the spin lattice relaxation time (T1) which is of great interest.

After pausing for the recovery time $\tau_i$, a 90° pulse is applied to the formation, causing the spins which have relaxed somewhat (according to the decay T1) to tip into the measurement plane where they generate a free induction decay (FID) signal in the measurement coil of the borehole tool. Because the deadtime of the borehole tool is on the order of fifty microseconds which is longer than the free induction decay time, the FID is not observed. However, by using the 90° pulse as the first pulse in a Carr-Purcell-Meiboom-Gill sequence, as explained below, indications of T1 and T2 are obtained.

At a time $\tau_{cp}$ (Carr-Purcell time) after the 90° pulse, a 180° pulse is applied, and as seen in FIG. 3a, further 180° pulses (known as refocusing pulses) are applied every $2\tau_{cp}$ in accord with the CPMG sequence. These 180° pulses generate measurable echoes at times $\tau_{cp}$ after each refocusing pulse. As indicated in FIG. 3c, the magnitude of the echoes decays over a period of time. The rate of decay is dictated by the spin-spin or T2 relaxation parameter. By applying many 180° pulses, numerous echo points are available for providing a decay curve indicative of T2. T2 has been shown to be empirically related to T1 in certain rock types and is therefore also of greart interest to the well log analyst.

In order to maximize the signal from the tipped nuclei, the RF pulses are always transmitted at maximum power, typically a few kilowatts, which leads to the condition that the 90° pulse is typically half the duration of the 180° refocusing pulse (assuming that the pulses have a substantially square shaped envelope, necessary for maintaining maximum bandwidth). In one embodiment of the invention, 180° refocusing pulses, such as in a conventional CPMG sequence are used.

Copending application Ser. No. 09/551,761 filed on Apr. 18, 2000 and U.S. Pat. No. 6,163,153 to Reiderman et al., the contents of which are fully incorporated herein by reference, disclose the use of refocusing pulses different from 180° to reduce the power consumption and improve the signal-to-noise ratio of the NMR signals. They point out that in a conventional CPMG sequence, the RF pulse has twice the bandwidth of the 180° pulse. As a result of this, only about half the nucleii which are tipped by the 90° pulse are subsequently refocused by the 180° pulse. The '761 application and Reiderman teach the use of pulse sequences in which the refocusing pulses have a shorter duration than a 180° pulse. With these refocusing pulses, it is possible to shorten the length of the NMR pulse sequences, so that the effect of tool motion is reduced simply due to the shorter duration of the acquisition time.

Pulse sequences are usually applied in phase-alternated pairs (PAPs) to remove systematic noise, such as "ringing" signals, arising from the decay of RF energy stored in the tool structure, baseline arefacts and the like. Various phase alternation schemes are possible, but in the simplest the phase of the tipping pulses is inverted in the second sequence of a PAP and the data from the two sequences is added. Correct functioning of the phase alternation scheme relies on the repeatability of the systematic noise signals.

Turning now to FIG. 4, a major problem with the use of MWD tools for NMR measurements is discussed. Shown is a cross section of a borehole 312 having a drilling tool 313 therein. Due to various reasons such as misalignment, mass imbalance, inhomogeneity in the physical properties of the rock drilled and/or the excitation of the drillstring caused by contact with the borehole wall, the drill string will exhibit dynamic vibrations that may have a combination of axial, torsional and whirling motions. The rotational motion of the drillstring by itself has little effect on the formation of NMR echoes because the magnetic field produced by the magnets in the preferred embodiment are rotationally symmetric and consequently the NMR measurement is invariant to rotational motion, as described above. The axial and whirling motions of the drillstring however are detrimental to the performance of an NMR tool: the magnetic fields produced by the NMR tool vary axially and radially so axial and radial motion of the tool with respect to the formation results in an effective time dependence in the tool's static field as seen by the nuclear spins in the formation fluids, so the NMR measurement is adversely affected by motion in those directions.

The motion of the NMR tool during the initial tipping pulse and subsequent spin system evolution in particular determines the data quality. Neglecting rotational motion, the tool motion has three components: parallel, perpendicular and azimuthal to the tool axis, i.e., axial, radial and rotational motion respectively.

Axial motion is determined both by the rate of penetration, and the axial vibration of the drillstring. Radial motion is determined solely by the radial motion of the drillstring. Azimuthal motion has no effect upon the NMR measurement using the acquisition system described above where the static field has complete rotational symmetry.

The motion of the tool is measured by suitable motion sensors, such as accelerometers, magnetometers or gyroscopes or combinations thereof. These sensors may be placed at any suitable location on the drilling tool in the proximity of the magnet and coil arrangement. The wait period in a pulse sequence may be extended slightly without affecting the data quality and this feature may be used to delay the application of the tipping pulse until a suitable state of tool motion is achieved. The trigger may be obtained by monitoring the motion sensor signals. Suitable states for triggering are instantaneous moments when the tool is stationary, or if the motion has a strong periodic component, then subsequent pulse sequences may be triggered to synchonize with this motion. Such motion triggered pulsing will improve the NMR spin-echo formation.

In addition, it has been found that the ringing signal artifacts vary according to the stresses and strains imposed on the sensor structure. This is because the ringing signals are associated with RF energy being dissipated in the magnetic and conducting elements of the tool structure. The correct cancellation of ringing artifacts therefore relies on the tool structure being in the same state of strain during each of the two pulse-echo trains in a phase alternated pair. This may be achieved by the motion triggered pulsing scheme described above.

Another aspect of the present invention is the use of a processor downhole to predict the motion of the tool using measurements of the tool motion. One such example of a predictive filter is disclosed in U.S. Pat. No. 5,784,273 issued to Madhavan, that shows the use of a Kalman filter to predict the motion of the spindle of a machine tool. Thus, as an alternative to triggering data acquisition based upon the tool motion, the present invention includes the option to trigger data acquisition based upon the predicted tool motion. One embodiment of the present invention includes the use of a predictive filter to predict the motion of the tool, and trigger data acquisition upon both the predicted motion and the criteria for optimal conditions for data acquisition discussed above. In one embodiment of the invention, the predictive filter is a Kalman filter. In another embodiment of the invention, a predictive filter based upon spectral analysis of the tool motion is used instead of, or in addition to, the Kalman filter.

The dynamics of the tool motion are quite complicated and under certain circumstances, it may be possible to decouple the axial motion due to tool bounce from the transversal motion. Under these circumstances, two different filters may be employed.

A typical NMR measurement is obtained by signal averaging a number of data acquisitions to improve the signal to noise ratio. In the case of motion containing one or more periodic components, using the output of the predictive filter, each of those data acquisitions can be triggered when the NMR tool is in approximately the same position, stationary or in the same state of motion, and the data averaged to improve the signal to noise ratio.

Referring again to FIG. 4, the center of the borehole 312 is shown at 310 while the center of the drillstring is at 314. The drillstring has a radius $r_0$ and the motion of the center of the drillstring may be approximated by a circle of radius $R_c$. As noted above, the present invention has a static magnetic field that has complete rotational symmetry. The simplest situation for the drillstring 313 is a steady state centralized rotation represented by $R_c(t)=0$, and $\theta(t)=A+\omega t$, where $\omega$ is the angular speed of the drillstring. Under these conditions, the magnetic field applied to a given volume of the formation is time invariant. This is the best situation for an NMR tool. The initial tipping pulse can be applied at any time and the best possible data can be acquired. While this steady state centralized rotation is not likely to occur frequently, it is nevertheless a desirable time for initiating and acquiring the pulse sequence.

For the case of radial vibration with a singular characteristic angular frequency $\omega_{vib}$, the radius $R_c(t)=C \sin(\omega_{vib}t+\phi)$, and data acquisition may be triggered when, e.g., $dR_c(t)/dt=0$, i.e., there is no radial component of drillstring motion. Radial vibration with a single characteristic angular frequency is not likely to occur frequently, and a superposition of vibrational modes are likely to be observed. However, even when multiple vibrational modes are present, the best time to trigger data acquisition would be when this condition, i.e., $dR_c(t)/dt=0$, is satisfied. This condition may be predicted by the prediction filters noted above, e.g., based upon spectral analysis or by Kalman filtering.

The case of radial vibration at a single characteristic frequency exemplifies another aspect of the invention, namely the dynamic control of the pulse sequence parameters to optimize the data acquired, and enables a simple explanation. By adjusting the parameter $t_{cp}$ to equal $2\pi/\omega_{vib}$, or a multiple thereof, the effect of vibration upon the modulation of the data acquired is minimized. For the more usual case where a superposition of vibrational modes are observed, the parameter $t_{cp}$ can be set for the principal component of the vibration spectrum.

This is illustrated in FIG. 5. A series of pulse echos 407a, 409a, 411a, 413a, 415a are shown with a constant echo interval of $t_{CP}$ for the time intervals between the refocusing pulses. The abscissa 401 is time and the ordinate is the pulse echo amplitude. Due to radial tool movement, the peaks of the pulse echos do not fall on the curve 405 which defines, e.g., a single decaying exponential with a relaxation time $T_2$. In prior art methods, any deviation of the peaks of the pulses 407a, 409a, 411a, 413a, 415a would be interpreted as noise on the data and an improper decay time would be determined. With the present invention, the timing of the pulses may be non-uniform and the pulse echoes 407b, 409b, 411b, 413b, 415b would give a better estimate of the relaxation time $T_2$.

Knowledge of the tool motion and control of the pulse sequence and the data acquisition parameters make it possible to improve the data quality, i.e., increase the signal-to-noise ratio.

The signals obtained by the method described above may be processed by a downhole processor or, alternatively, may be processed at an uphole location. When an uphole processor is used, the data are preferably stored downhole and processed when the drilling assembly is brought back up to the surface: present day telemetry capabilities are not adequate to send the data for processing uphole.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of determining a parameter of interest of a volume of earth formation surrounding a borehole with a borehole tool conveyed on a drilling tubular having a drill bit thereon for drilling the borehole, the method comprising:
   (a) using a magnet assembly on the borehole tool to produce a static magnetic field having a substantially uniform field strength in said volume of the formation;
   (b) using a plurality of sensors on the borehole to provide a motion signal indicative of motion of the tool in the borehole;
   (c) applying a predictive filter to the motion signal giving a predicted motion signal,
   (d) activating a transmitter on the borehole tool in response to said predicted motion signal to produce a radio frequency (RF) magnetic field having a direction substantially orthogonal to a direction of the static field in said volume of the formation,
   (e) measuring with the borehole tool signals induced by the RF field in the formation to give at least one measured signal; and
   (f) processing the at least one measured signal using a processor to determine the parameter of interest.

2. The method of claim 1 wherein activating the transmitter further comprises using a processor on the borehole tool for processing said motion signal to give the predicted motion signal and activating the transmitter at a time when said predicted motion signal is indicative of a desired motion of the tool.

3. The method of claim 2 wherein the desired tool motion is at least one of (i) substantially zero radial velocity of motion of the tool, (ii) an axial velocity of the tool that is less than a predetermined value, (iii) a radial displacement of the tool that is less than a predetermined value, (iv) a radial velocity of the tool that is less than a predetermined value, and, (v) a combination of radial velocity and axial velocity of the tool that is less than a predetermined value.

4. The method of claim 1 wherein the predictive filter is at least one of (i) a filter based upon spectral analysis, and (ii) a Kalman filter.

5. The method of claim 4 wherein the RF magnetic field is a pulsed field including at least a first pulse sequence:

$$90-\tau_1-(R-\tau_2-\text{echo}-\tau_2)_j$$

wherein 90 is a tipping pulse for tipping nuclear spins of nuclei within the region of examination at an angle substantially equal to ninety degrees to cause precession thereof, $\tau_1$ and $\tau_2$ are wait times, R is a refocusing pulse, and j=1, 2, . . . J, and J is the number of echoes collected in a single sequence of pulses; wherein at least one of (i) the time of the tipping pulse, (ii) the wait time $\tau_1$, (iii) the wait time $\tau_2$, and, (iv) the time of the refocusing pulse, are related to the motion signal.

6. The method of claim 5 wherein the refocusing pulse is selected from the group consisting of (i) a 180° pulse, and, (ii) a pulse that refocuses more of the precessing nuclear spins than a 180° pulse.

7. The method of claim 6 wherein at least one of (i) the time of the tipping pulse, (ii) the wait time $\tau_1$, (iii) the wait time $\tau_2$, and, (iv) the time of the refocusing pulse, are related to the motion signal.

8. The method of claim 1 wherein said plurality of sensors comprise sensors selected from (i) accelerometers, (ii) magnetometers, and (iii) gyroscopes.

9. The method of claim 1 wherein the RF magnetic field is a pulsed field including at least a first pulse sequence:

$$90-\tau_1-(R-\tau_2-\text{echo}-\tau_2)_j$$

wherein 90 is a tipping pulse for tipping nuclear spins of nuclei within the region of examination at an angle substantially equal to ninety degrees to cause precession thereof, $\tau_1$ and $\tau_2$ are wait times, R is a refocusing pulse, and j=1, 2, . . . J, and J is the number of echoes collected in a single sequence of pulses.

10. The method of claim 9 wherein in the at least first pulse sequence said tipping pulse is a 90(+x) pulse, the pulsed field further comprising a second pulse sequence wherein said tipping pulse is a 90(−x) pulse, where +x and −x denote the phase of the radio frequency carrier of the pulse with respect to a continuous radio frequency signal of the same frequency, and wherein results measured in the first and second pulse sequence are subtracted from each other to provide a corrected measurement.

11. The method of claim 9 wherein at least one of (i) the time of the tipping pulse, (ii) the wait time $\tau_1$, (iii) the wait time $\tau_2$, and, (iv) the time of the refocusing pulse, are related to the predicted motion signal.

12. The method of claim 1 wherein the processor is located on the borehole tool.

13. A method for determining parameter of interest of a volume of earth formation surrounding a borehole with a borehole tool conveyed on a drilling tubular having a drill bit thereon for drilling the borehole, the method comprising:
(a) using a magnet assembly on the borehole tool to produce a static magnetic field having a substantially uniform field strength in said volume of the formation;
(b) using a plurality of sensors on the borehole to provide a motion signal indicative of motion of the tool in the borehole;
(c) determining from said motion signal a frequency of radial motion of the tool within the borehole;
(d) activating a transmitter on the borehole tool with a pulsed radio frequency (RF) magnetic field wherein times of said pulses are determined in part by said determined frequency;
(e) measuring with the borehole tool signals induced by the RF field in the formation to give at least one measured signal; and
(f) processing the at least one measured signal using a processor to determine the parameter of interest.

14. The method of claim 13 wherein determining said frequency further comprises applying a predictive filter to the motion signal giving a predicted motion signal, and activating the transmitter further comprises using said predicted motion signal.

15. The method of claim 14 wherein the predictive filter is at least one of (i) a filter based upon spectral analysis, and (ii) a Kalman filter.

16. The method of claim 13 wherein said RF field comprises a tipping pulse and a plurality of refocusing pulses, the method further comprising determining time intervals between consecutive ones of said refocusing pulses based upon said motion signal.

17. The method of claim 16 wherein the refocusing pulses are selected from the group consisting of (i) a 180° pulse, and, (ii) a pulse that refocuses more of the precessing nuclear spins than a 180° pulse.

* * * * *